United States Patent
Li et al.

(10) Patent No.: US 12,163,942 B2
(45) Date of Patent: Dec. 10, 2024

(54) CROP GROWTH INFORMATION MONITORING METHOD AND DEVICE AND METHOD FOR MANUFACTURING A CROP GROWTH INFORMATION MONITORING DEVICE

(71) Applicant: Agricultural Information Institute of Chinese Academy of Agricultural Sciences, Beijing (CN)

(72) Inventors: Denghua Li, Beijing (CN); Shiwei Xu, Beijing (CN); Ganqiong Li, Beijing (CN); Wei Chen, Beijing (CN)

(73) Assignee: AGRICULTURAL INFORMATION INSTITUTE OF CHINESE ACADEMY OF AGRICULTURAL SCIENCES, Beijing (CN)

( * ) Notice: Subject to any disclaimer, the term of this patent is extended or adjusted under 35 U.S.C. 154(b) by 0 days.

(21) Appl. No.: 17/442,350

(22) PCT Filed: Oct. 26, 2020

(86) PCT No.: PCT/CN2020/123578
§ 371 (c)(1),
(2) Date: Sep. 23, 2021

(87) PCT Pub. No.: WO2021/248772
PCT Pub. Date: Dec. 16, 2021

(65) Prior Publication Data
US 2023/0090813 A1 Mar. 23, 2023

(30) Foreign Application Priority Data
Jun. 11, 2020 (CN) .......................... 202010530747.3

(51) Int. Cl.
*G01N 33/00* (2006.01)
*G01N 27/12* (2006.01)
(Continued)

(52) U.S. Cl.
CPC ....... *G01N 33/0098* (2013.01); *G01N 27/127* (2013.01); *H01L 21/02568* (2013.01); *H01L 21/288* (2013.01)

(58) Field of Classification Search
CPC ............ G01N 33/0098; G01N 27/127; G01N 27/125; H01L 21/02568; H01L 21/288
See application file for complete search history.

(56) References Cited

U.S. PATENT DOCUMENTS

2019/0388869 A1   12/2019   Martin et al.

FOREIGN PATENT DOCUMENTS

| CN | 1115848 A | 1/1996 |
|---|---|---|
| CN | 105072887 A | 3/2014 |

(Continued)

OTHER PUBLICATIONS

Waybackmachine UCI Cleaning Procedures for Silicon Wafers, Sep. 7, 2015 (Year: 2015).*

(Continued)

*Primary Examiner* — Timothy P Graves
(74) *Attorney, Agent, or Firm* — Epstein Drangel LLP; Robert L. Epstein

(57) ABSTRACT

Provided are a crop growth information monitoring method and device and a method for manufacturing a crop growth information monitoring device. The crop growth information monitoring device includes an air exchange channel support, a crop information sensing sensitive layer, an electrode, and a substrate. The air exchange channel support is disposed on the substrate, and in a case where the air exchange channel support is in contact with a monitoring point on a surface of a crop, a gas exchange channel is formed between the crop information sensing sensitive layer and the surface of the crop. The crop information sensing sensitive layer is configured to sense information about (Continued)

molecules emitted through crop transpiration so as to generate a molecule concentration capture signal. The electrode is plated on an upper surface of the substrate, and the crop information sensing sensitive layer is coated on the electrode.

8 Claims, 9 Drawing Sheets

(51) Int. Cl.
  *H01L 21/02* (2006.01)
  *H01L 21/288* (2006.01)

(56) References Cited

FOREIGN PATENT DOCUMENTS

| | | | | |
|---|---|---|---|---|
| CN | 103910354 A | 7/2014 | | |
| CN | 104713915 A | 6/2015 | | |
| CN | 105036121 A | 11/2015 | | |
| CN | 105466979 A | 4/2016 | | |
| CN | 205193001 U | 4/2016 | | |
| CN | 107741444 A | 2/2018 | | |
| CN | 207408333 U | 5/2018 | | |
| CN | 207516297 U | 6/2018 | | |
| CN | 207675686 U | 7/2018 | | |
| CN | 110146555 A | * | 8/2019 | ........... G01N 27/125 |
| CN | 111220496 A | 6/2020 | | |
| CN | 111693578 A | 9/2020 | | |
| JP | 2009115671 A | 5/2009 | | |
| WO | 2018116029 A1 | 6/2018 | | |

OTHER PUBLICATIONS

First Office Action of priority Chinese patent application No. 202010530747.3 filed on Jun. 11, 2020 (Original and English Translation).
First Search Report of priority Chinese patent application No. 202010530747.3 filed on Jun. 11, 2020.
International Search Report of PCT/CN2020/123578, filed Oct. 26, 2020.
Seval Oren, Halil Ceylan, Patrick S. Schnable, Liang Dong High-Resolution Patterning and Transferring of Graphene-Based Nanomaterials onto Tape toward Roll-to-Roll Production of Tape-Based Wearable Sensors Advanced Materials Technologies vol. 2, Issue 12 First published: Nov. 17, 2017.
Seval Oren, Zhaokui Wang, Xinran Wang, Shawana Tabassum, Yueyi Jiao, 1 Byron J. Montgomery, Nathan Neihart, Colton M. Mcninch, Patrick S. Schnable, and Liang Dong Tracking of water movement dynamics inside plants using leaf surface humidity sensors Proceedings of the 12th IEEE International Conference on Nano/Micro Engineered and Molecular Systems Apr. 9-12, 2017, Los Angeles, USA.

* cited by examiner

CROP GROWTH INFORMATION MONITORING METHOD AND DEVICE AND METHOD FOR MANUFACTURING A CROP GROWTH INFORMATION MONITORING DEVICE

CROSS-REFERENCE TO RELATED APPLICATIONS

This is a National Stage Application, filed under 35 U.S.C. 371, of International Patent Application No. PCT/CN2020/123578, filed on Oct. 26, 2020, which claims priority to Chinese Patent Application No. 202010530747.3 filed with the CNIPA on Jun. 11, 2020, the disclosures of which are incorporated herein by reference in their entireties.

TECHNICAL FIELD

The present disclosure relates to the technical field of agricultural information, for example, a crop growth information monitoring method and device and a method for manufacturing a crop growth information monitoring device.

BACKGROUND

With the advent of the era of the Internet of Things, big data and artificial intelligence, agriculture is moving towards intelligent production and unmanned operation. Data acquisition and information monitoring are the foundation of agricultural information technologies and support analysis and decision-making, intelligent control, and information service.

A crop growth monitoring method includes remote sensing monitoring, machine vision image analysis and processing, hyperspectral analysis, chlorophyll fluorescence spectrum analysis and detection, infrared detection, and the like. The method is used for acquiring apparent information such as the plant height, stem, fruit size and leaf thickness of a crop and internal stem flow, chlorophyll and leaf area index so as to guide fertilization, irrigation and agricultural operations. It is difficult to monitor crop life information by using a traditional crop growth information monitoring method, which is not conducive to the accurate and dynamic monitoring of crop growth information. Moreover, a monitoring device is expensive, which is not conducive to the large-scale popularization and application of technologies.

SUMMARY

The present disclosure provides a crop growth information monitoring method and device and a method for manufacturing a crop growth information monitoring device, which can nondestructively monitor life information in a crop growth process online.

A crop growth information monitoring device is provided and includes an air exchange channel support, a crop information sensing sensitive layer, an electrode, and a substrate.

The air exchange channel support is disposed on the substrate, and in a case where the air exchange channel support is in contact with a monitoring point on a surface of a crop a gas exchange channel is formed between the crop information sensing sensitive layer and the surface of the crop.

The crop information sensing sensitive layer is configured to sense information about a molecule emitted through crop transpiration so as to generate a molecule concentration capture signal.

The electrode is plated on an upper surface of the substrate, and the crop information sensing sensitive layer is coated on the electrode.

A method for manufacturing a crop growth information monitoring device is further provided and includes the steps described below.

A substrate is acquired.

An electrode is plated on the upper surface of the substrate.

A crop information sensing sensitive material is coated on the electrode so as to form a crop information sensing sensitive layer, where the crop information sensing sensitive layer is configured to sense information about a molecule emitted through crop transpiration so as to generate a molecule concentration capture signal.

Heat treatment is performed on the substrate.

An air exchange channel support is mounted on the upper surface of the substrate, and in a case where the air exchange channel support is in contact with a monitoring point on a surface of a crop, a gas exchange channel is formed between the crop information sensing sensitive layer and the surface of the crop.

The method further includes: acquiring an electrical parameter signal collection module and establishing an electrical connection between the electrical parameter signal collection module and the electrode; acquiring a signal conditioning circuit module, disposing the signal conditioning circuit module on a lower surface of the substrate, and establishing an electrical connection between the signal conditioning circuit module and the electrical parameter signal collection module; and acquiring a power supply module.

A crop growth information monitoring method is further provided and includes the following steps: attaching and mounting the crop growth information monitoring device provided in the embodiment of the present disclosure to a surface of crop tissue and sensing information about a molecule released by the crop tissue through a crop information sensing sensitive layer of the crop growth information monitoring device so as to generate a molecule concentration capture signal.

DETAILED DESCRIPTION

Figure 1:
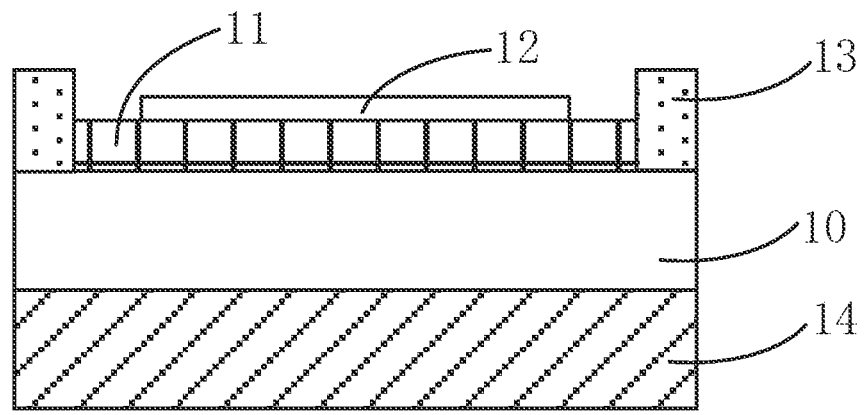
FIG. 1 is a sectional diagram of a crop growth information monitoring device according to embodiment one of the present disclosure.

The present disclosure is described below in conjunction with the drawings and embodiments. Only part, not all, of the structures related to the present disclosure are illustrated in the drawings.

Embodiment One

FIG. 1 is a sectional diagram of a crop growth information monitoring device according to embodiment one of the present disclosure. As shown in FIG. 1, the crop growth information monitoring device includes an air exchange channel support 13, a crop information sensing sensitive layer 12, an electrode 11, and a substrate 10.

The air exchange channel support 13 is disposed on the substrate 10, so that when the air exchange channel support 13 is in contact with a monitoring point on a surface of a crop, a gas exchange channel is formed between the crop information sensing sensitive layer 12 and the surface of the crop.

The crop information sensing sensitive layer 12 is configured to sense information about a molecule emitted through crop transpiration so as to generate a molecule concentration capture signal such as a water-molecule concentration capture signal, an oxygen-molecule concentration capture signal, and/or a carbon dioxide-molecule concentration capture signal. The molecule concentration capture signal is the sensed information about the molecule.

The electrode 11 is plated on an upper surface of the substrate 10, and the crop information sensing sensitive layer 12 is coated on the electrode 11.

In an embodiment, the crop information sensing sensitive layer 12 may be a functionalized graphene oxide layer; the electrode 11 is a metal electrode and may be an interdigital electrode, and the metal may be gold, silver, aluminum, or an alloy thereof. In an embodiment, the crop information sensing sensitive layer 12 may be made of a novel functionalized two-dimensional nano material, is coated on the electrode 11, and is configured to sense and capture information about the water molecule emitted through the crop transpiration. In this embodiment, an electrode element is a hyperfine electrode circuit formed by nanotechnology processing and plated on the upper surface of the substrate 10 (which may be a flexible substrate) for generating and transmitting sensor electrical signals, that is, for sensing the information about a molecule emitted through crop transpiration so as to generate a molecule concentration capture signal.

In an embodiment, the air exchange channel support 13 may be disposed on the upper surface of the substrate 10, and the electrode 11 is plated on the upper surface of the substrate 10 but does not completely cover the upper surface of the substrate 10, so the air exchange channel support 13 may be disposed on a position of the upper surface of the substrate 10 where no electrode is plated.

In this embodiment, the substrate 10 may be a flexible printed circuit (FPC), a polyimide film, a polyester film, a flexible film, a silicon wafer, a silicon dioxide wafer, a ceramic wafer, or another material.

In this embodiment, the air exchange channel support 13 may include at least two supporting units disposed around the electrode 11; in an embodiment, the air exchange channel support 13 includes two supporting strips which are respectively located on two sides of the electrode 11 or on two sides of the upper surface of the substrate 10 so that when the crop growth information monitoring device is attached and mounted to the surface of a monitored crop tissue, the air exchange channel support 13 is in contact with a monitoring point of the crop and an air exchange channel is formed between the crop information sensing sensitive layer 12 and the surface of the crop.

Figure 2A:
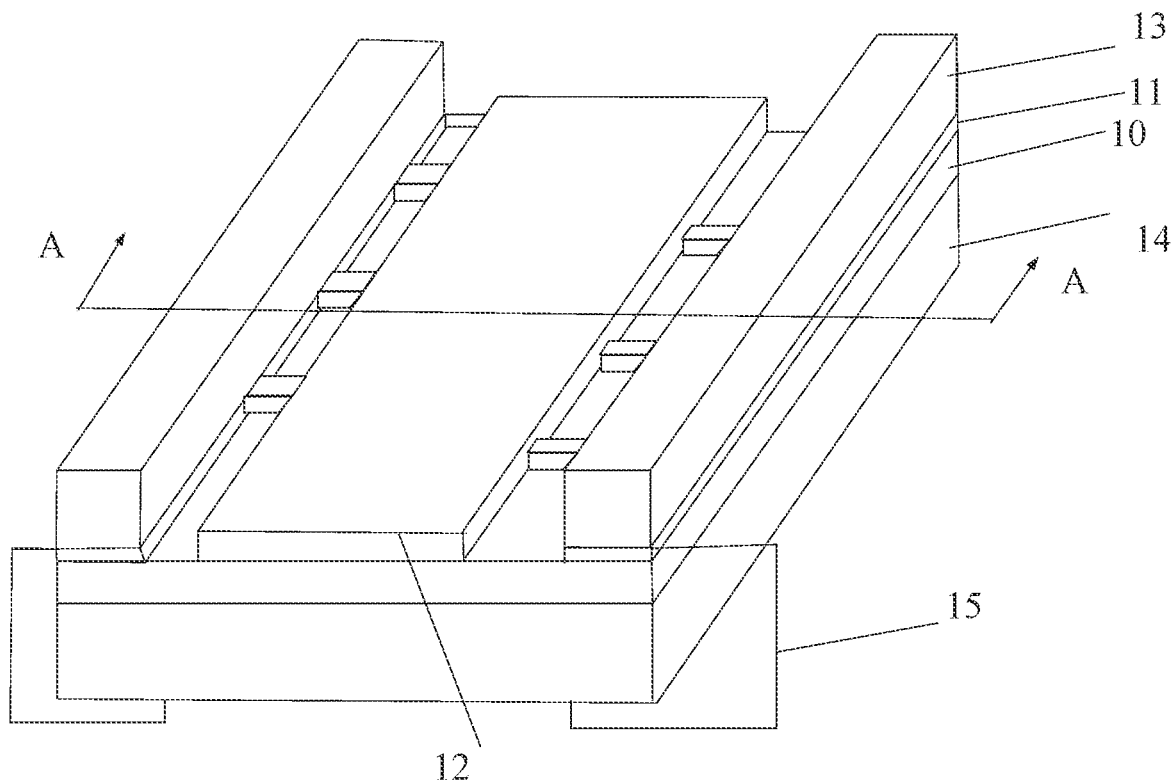
FIG. 2A is a perspective diagram of another crop growth information monitoring device according to embodiment one of the present disclosure.
Figure 2B:
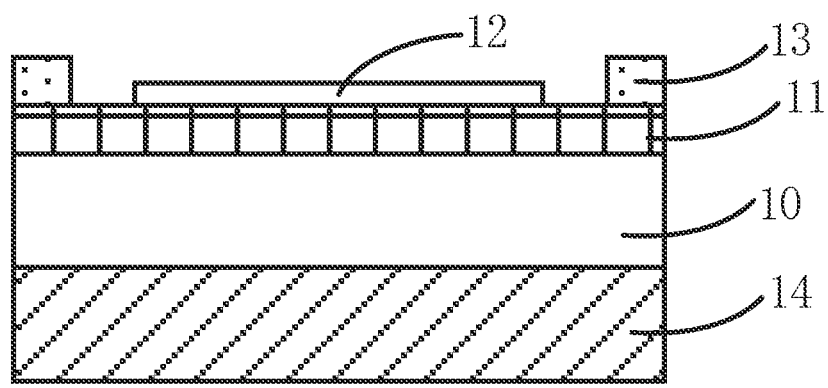
FIG. 2B is a sectional diagram of the crop growth information monitoring device in FIG. 2A along the line A-A.

In an embodiment, the air exchange channel support 13 may also be disposed on an upper surface of the electrode 11, as shown in FIGS. 2A to 2B, and if the electrode 11 completely covers the upper surface of the substrate 10, the air exchange channel support 13 may be disposed on the upper surface of the electrode 11. As long as the upper surface of the air exchange channel support 13 is higher than the upper surface of the crop information sensing sensitive layer 12, when the upper surface of the air exchange channel support 13 is in contact with the monitoring point on the surface of the crop, an air channel is formed between the crop information sensing sensitive layer 12 and the surface of the crop so that when the crop growth information monitoring device is attached and mounted to the surface of the monitored crop tissue, the air exchange channel support 13 is in contact with the monitoring point of the crop and the air exchange channel is formed between the crop information sensing sensitive layer 12 and the surface of the crop.

Figure 3:
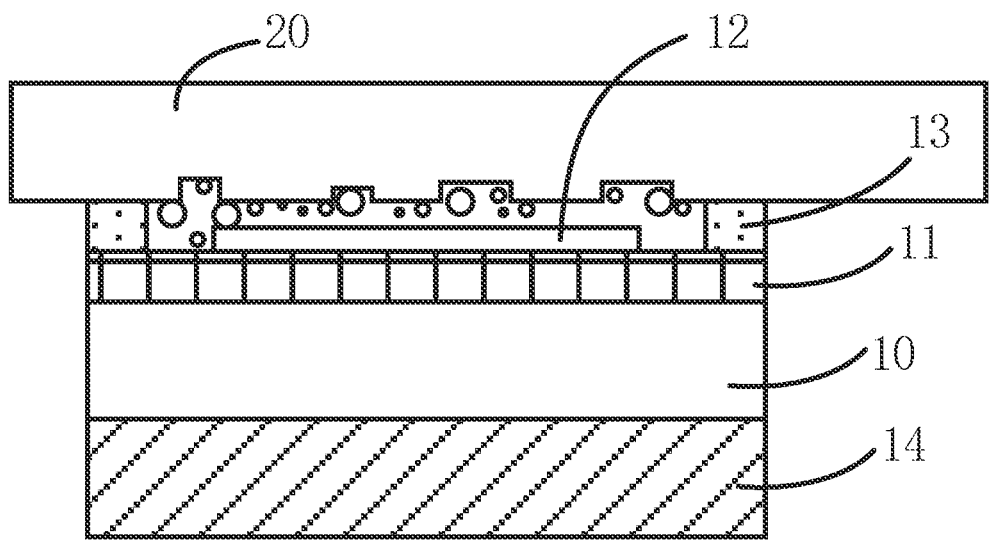
FIG. 3 is a diagram illustrating a usage scenario of a crop growth information monitoring device according to embodiment one of the present disclosure.

FIG. 3 is a diagram illustrating a usage scenario of a crop growth information monitoring device according to embodiment one of the present disclosure. As shown in FIG. 3, during monitoring, the monitoring device is placed on the surface of crop 20, the air exchange channel support 13 is in direct contact with the crop 20, and an air channel exists between the crop information sensing sensitive layer 12 and the surface of the crop 20, which is conducive to the exchange of air in the channel with the outside air, avoids sealing the surface of the crop 20 and thus avoids causing the water-molecule accumulation. The crop information sensing sensitive layer 12 is configured to collect a molecule concentration capture signal of crop 20, that is, a corresponding electrical signal may be generated according to the concentration of the water molecule on the surface of the crop.

The molecule concentration capture signal of the crop collected by the crop information sensing sensitive layer 12 may be transmitted to external equipment through the electrode 11. In this embodiment, the crop information sensing sensitive layer 12 not only detects and captures water molecules but also may perform functional modification and cutting on a targeted chemical group and combine different modification groups according to a transformation of a sensed object or a sensing parameter index so as to simultaneously and nondestructively detect and capture one or more of the following pieces of information of the crop tissue: nutrition information, hormone release information, information about volatile organic compounds (VOCs), or pesticide residue information.

The embodiments of the present disclosure provide a crop growth information monitoring method and device and a method for manufacturing a crop growth information monitoring device. The crop growth information monitoring device includes the air exchange channel support, the crop information sensing sensitive layer, the electrode, and the substrate. The air exchange channel support is disposed on the substrate so that when the air exchange channel support is in contact with the monitoring point on the surface of the crop, the gas exchange channel is formed between the crop information sensing sensitive layer and the surface of the crop. The crop information sensing sensitive layer is configured to sense the information about the molecule emitted through crop transpiration so as to generate the molecule concentration capture signal. The electrode is plated on the upper surface of the substrate, and the crop information sensing sensitive layer is coated on the electrode. According to the device provided in the embodiments of the present disclosure, the air exchange channel support is mounted on the surface of the crop issue so that life information in the crop growth process can be nondestructively monitored online, and the device has the characteristics of large-scale production, low manufacturing cost, high monitoring precision, and intelligent monitoring of crop information.

Embodiment Two

Figure 4:
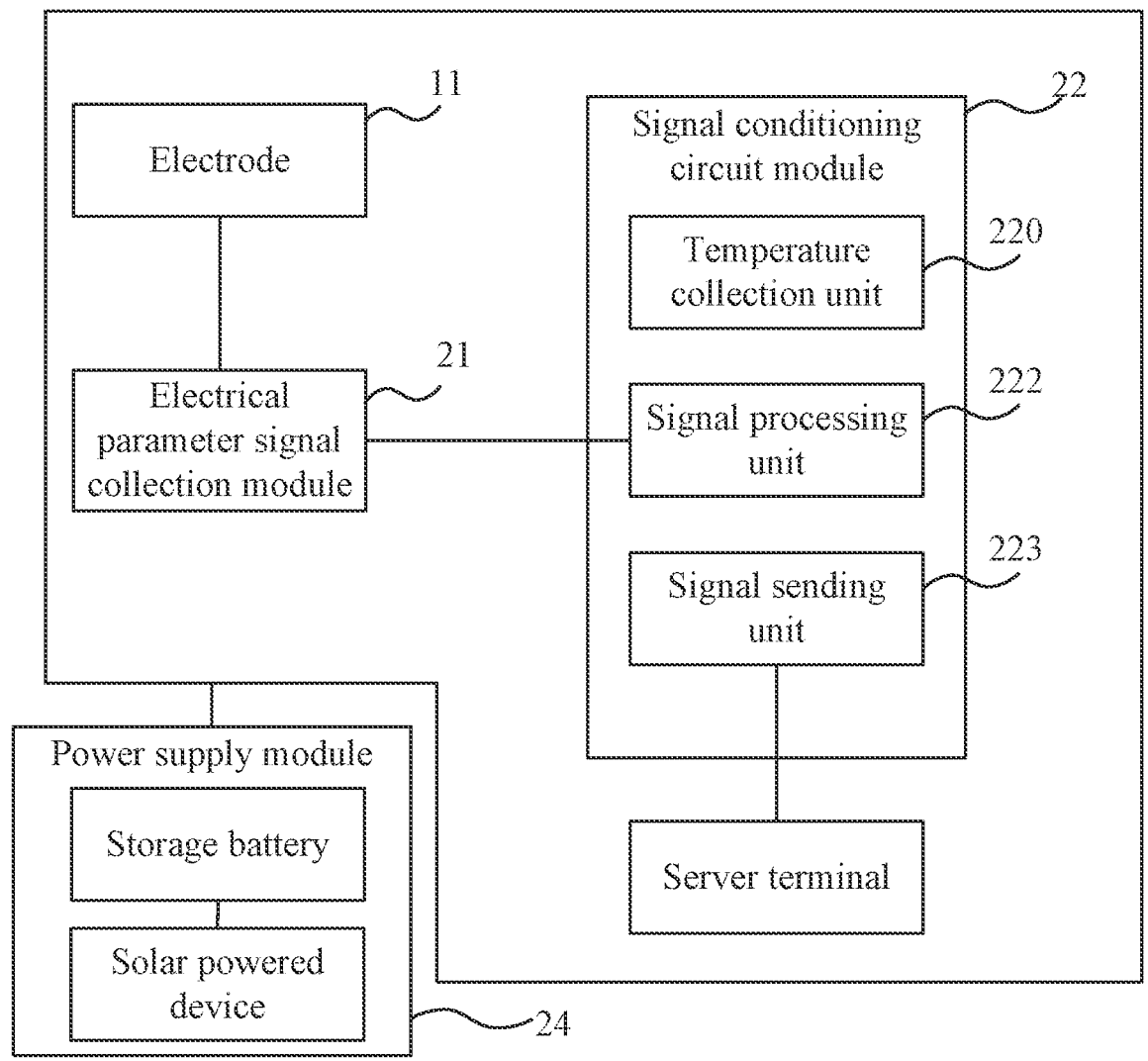
FIG. 4 is a diagram illustrating connections of modules of a crop growth information monitoring device according to embodiment two of the present disclosure.

FIG. 4 is a diagram illustrating connections of modules of a crop growth information monitoring device according to embodiment two of the present disclosure. On the basis of the preceding embodiment, in an embodiment, the crop growth information monitoring device further includes a circuit module, and the circuit module includes an electrical parameter signal collection module 21, a signal conditioning circuit module 22, and a power supply module 24.

The electrical parameter signal collection module 21 is configured to receive through the electrode 11 the molecule concentration capture signal collected by the crop information sensing sensitive layer 12 and convert the molecule concentration capture signal captured by the crop information sensing sensitive layer 12 into an electrical signal by using an electrical parameter-molecule concentration adsorption and desorption physical and chemical effect of the crop information sensing sensitive layer 12.

The signal conditioning circuit module 22 includes a temperature collection unit 220, a signal processing unit 222, and a signal sending unit 223. The temperature collection unit 220 is configured to collect a temperature of the monitoring point of the crop so as to generate a temperature signal. The signal processing unit 222 is configured to determine molecule concentration information from a pre-stored molecule concentration-electrical parameter-temperature information correspondence according to the molecule concentration capture signal, and the temperature signal collected by the temperature collection unit 220. The signal sending unit 223 is configured to send the molecule concentration information generated by the signal processing unit 222 to a server terminal.

The power supply module 24 includes a storage battery and a solar powered device. The solar powered device is configured to convert solar energy into electrical energy and store the electrical energy in the storage battery. The storage battery may supply power to the electrical parameter signal collection module 21 and the signal conditioning circuit module 22 of the circuit module.

In this embodiment, the electrical parameter signal collection module 21 may collect signals of alternating current impedance, direct current resistance, capacitance, inductance and resonance frequency of the crop information sensing sensitive layer 12. In this embodiment, the crop information sensing sensitive layer 12 not only detects and captures water molecules but also may perform functional modification and cutting on chemical groups according to an information transformation of a sensed object so as to nondestructively detect and capture one or more of the following pieces of information of the crop tissue: nutrition information, hormone release information, information about VOCs, or pesticide residue information.

The pre-stored molecule-electrical parameter-temperature information correspondence includes a correspondence among molecule concentration capture signals, temperature signals, and molecule concentration information (such as information about water molecules, oxygen molecules, carbon dioxide molecules, VOCs, pesticide residue, and hormone release). The molecule concentration capture signal is collected by the crop information sensing sensitive layer 12 and may actually be an alternating current impedance electrical signal or a direct current resistance signal. What is finally needed is the concentration information about molecules released by the crop. The molecule concentration information may include the moisture concentration of the crop or include the concentration of VOCs or other molecules released by the crop, so it is necessary to determine the corresponding molecule information according to the molecule concentration capture signal.

At different temperatures, the crop information sensing sensitive layer 12 of the crop growth information monitoring device is affected differently. Even in the case of the same molecule concentration, the crop information sensing sensitive layer 12 collects different molecule concentration capture signals at different temperatures, so it is necessary to determine the corresponding molecule information from the pre-stored molecule concentration-electrical parameter-temperature information correspondence according to the collected molecule concentration capture signal, and the temperature signal. The correspondence among a molecule concentration, an electrical parameter, and temperature information may be a three-dimensional curve or a three-dimensional curved surface about the molecule concentration capture signal, the temperature signal, and the molecule information.

The pre-stored molecule concentration-electrical parameter-temperature information correspondence may be made in the manner described below. The water molecule is used as an example, water molecule capture signals collected by the monitoring device at different temperatures and different water concentrations are recorded and calibrated. The three-dimensional curve or three-dimensional curved surface about the water-molecule capture signal, the temperature signal and the water-molecule information is made according to different temperatures, different water concentrations and correspondingly collected molecule concentration capture signals and is used as the pre-stored molecule concentration-electrical parameter-temperature information correspondence.

The signal sending unit 223 may be a wireless communication module, and the signal sending unit 223 may exemplarily be a Bluetooth module, a wireless-fidelity (Wi-Fi) module, or the like. The server terminal may be an operation terminal of an administrator and may be a smart phone, a tablet computer, or a background computer.

According to the embodiments of the present disclosure, the molecule concentration capture signal collected by the crop information sensing sensitive layer is received through the electrode, and the corresponding molecule information is determined from the pre-stored molecule concentration-electrical parameter-temperature information correspondence according to the molecule concentration capture signal, and the temperature signal collected by the temperature collection unit. In this manner, the corresponding molecule information is determined according to both the temperature signal and the molecule concentration capture signal, improving the accuracy of molecule information.

Embodiment Three

Figure 5A:
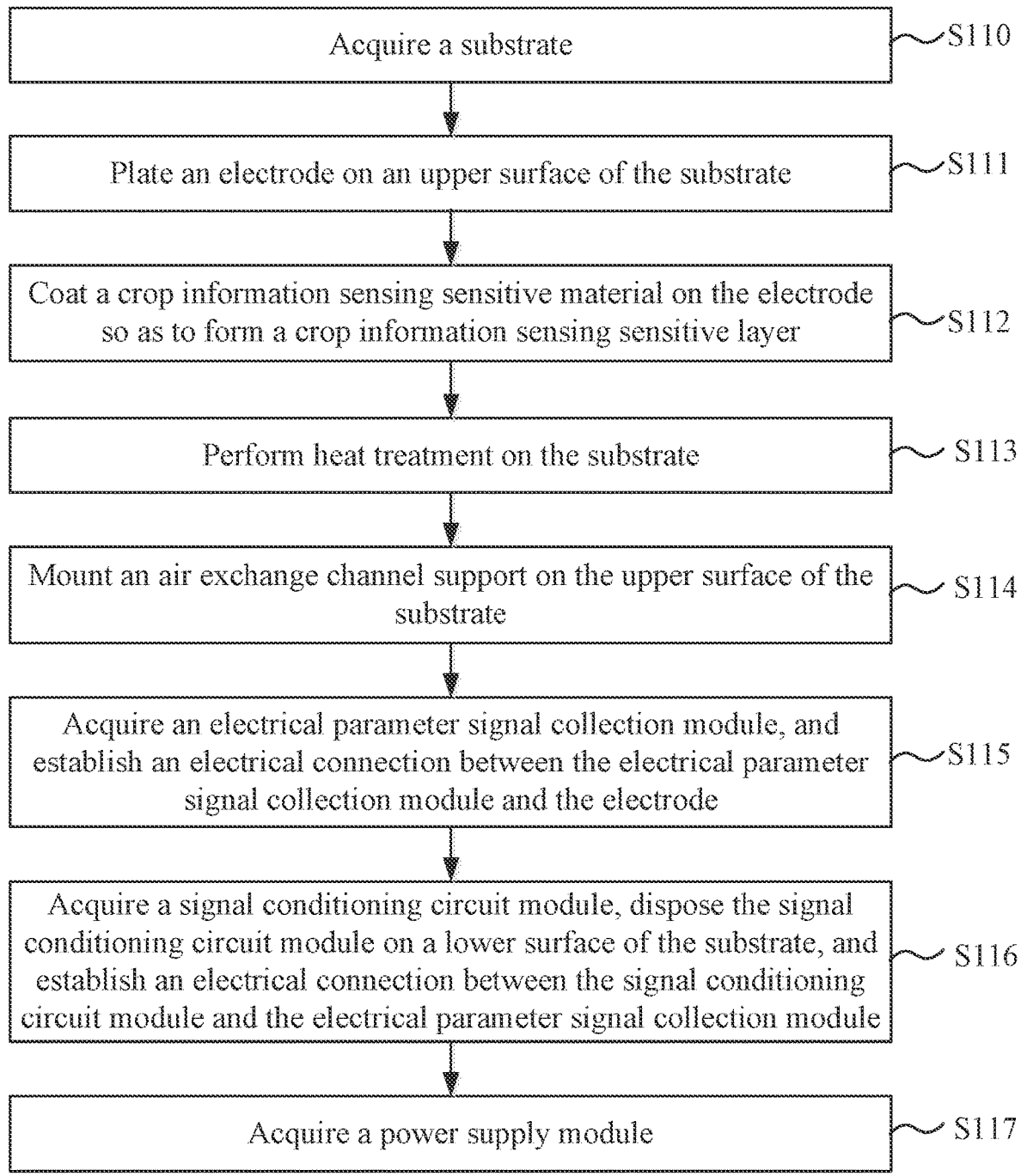
FIG. 5A is a flowchart of a method for manufacturing a crop growth information monitoring device according to embodiment three of the present disclosure.

FIG. 5A is a flowchart of a method for manufacturing a crop growth information monitoring device according to embodiment three of the present disclosure. On the basis of the preceding embodiments, as shown in FIG. 5, the method for manufacturing a crop growth information monitoring device includes S110 to S117.

In S110, a substrate is acquired. The substrate in this embodiment may be a flexible substrate. In an embodiment, the substrate may be one or more of an FPC, a polyimide film, a polyester film, a flexible film, a silicon wafer, a silicon dioxide wafer, a ceramic wafer, or another material.

In S111, an electrode is plated on the upper surface of the substrate. The electrode in this embodiment may form a hyperfine electrode circuit.

In S112, a crop information sensing sensitive material is coated on the electrode so as to form a crop information sensing sensitive layer. The water-molecule sensing sensitive material in this embodiment is a functionalized water-molecule sensing sensitive material prepared in advance, that is, a crop information sensing sensitive material which is a coatable or printable solution material. The crop information sensing sensitive layer not only detects and captures water molecules but may also perform functional modification and cutting on a targeted chemical group and combine different modification groups according to a transformation of a sensed object or a sensing parameter index so as to simultaneously and nondestructively detect and capture one or more of the following pieces of information of the crop tissue: nutrition information, hormone release information, information about VOCs, or pesticide residue information.

In an embodiment, the water-molecule sensing sensitive material may be a functionalized graphene oxide solution; correspondingly, before the water-molecule sensing sensitive material is coated on the electrode, the method further includes the operations described below.

Concentrated sulfuric acid and a sodium nitrate oxidant are added into an ice-water mixture, stirring is performed, and in a process of the stirring, graphite powder, potassium permanganate, a potassium permanganate catalyst, deionized water, and hydrogen peroxide are added to reduce a residual oxidant. Stirring is performed in water through an ultrasonic wave or high shear so as to obtain a single-layer graphene oxide suspension.

Centrifugal separation treatment, hydrochloric acid washing treatment, deionized water washing treatment, and filter cake vacuum drying treatment are performed on the single-layer graphene oxide suspension so as to obtain graphene oxide powder.

The graphene oxide powder is dissolved in deionized water, and functional modification and partial reduction treatment are performed on groups between plies so as to obtain a water-soluble functionalized graphene oxide solution as the water-molecule sensing sensitive material.

In an embodiment, the reduction treatment is to deoxidize the graphene oxide so as to reduce the graphene oxide to graphene; and the partial reduction treatment is to deoxidize part of the graphene oxide so as to reduce the part of the graphene oxide to graphene.

In S113, heat treatment is performed on the substrate.

In an embodiment, the substrate may be heated at 200° C. for 2 hours, or the substrate may be baked to be heated. After the heating treatment, the impurities and gases left in the substrate can be removed, which can improve the stability of the substrate. In an alternative embodiment, the heat treatment process may also be performed at a temperature of 110° C. for 3 hours.

In S114, an air exchange channel support is mounted on the upper surface of the substrate.

In S115, an electrical parameter signal collection module is acquired, and an electrical connection is established between the electrical parameter signal collection module and the electrode.

In S116, a signal conditioning circuit module is acquired and disposed on the lower surface of the substrate, and an electrical connection is established between the signal conditioning circuit module and the electrical parameter signal collection module.

In S117, a power supply module is acquired.

Figure 5B:
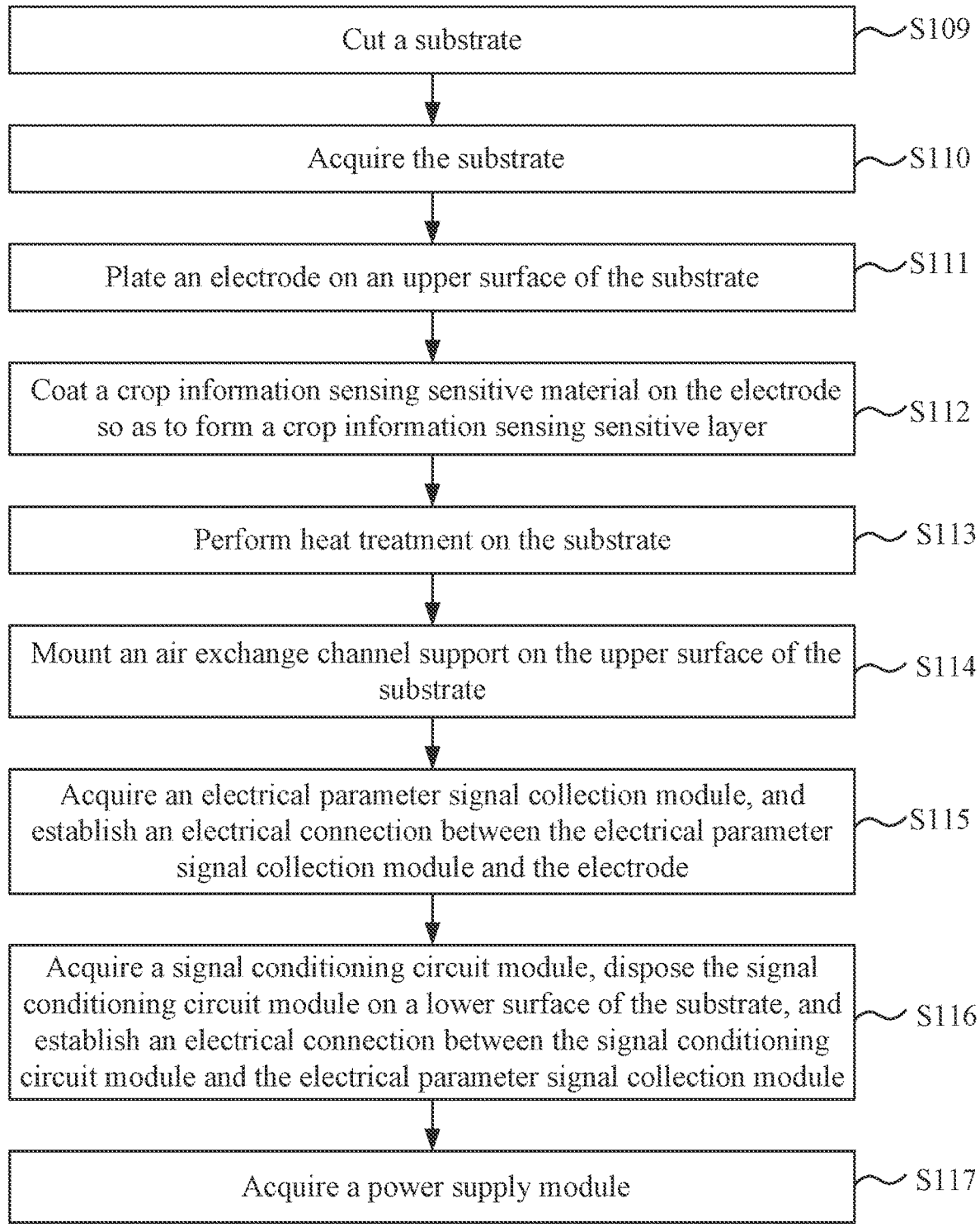
FIG. 5B is a flowchart of a method for manufacturing a crop growth information monitoring device according to an alternative of embodiment three of the present disclosure.

As shown in FIG. 5B, in an alternative embodiment, before step S110, the method includes S109 in which the substrate is cut, ultrasonic cleaning is performed by using acetone, absolute ethyl alcohol, and deionized water separately and nitrogen drying is performed. In the alternative embodiment, the substrate is cut to an appropriate size in advance, and the substrates of different sizes may be made according to different crops to which the monitoring devices are applied. Ultrasonic cleaning is performed in the deionized water so that impurities remained after the substrate is manufactured can be cleaned. In this manner, the stability of the substrate can be improved.

Figure 5C:
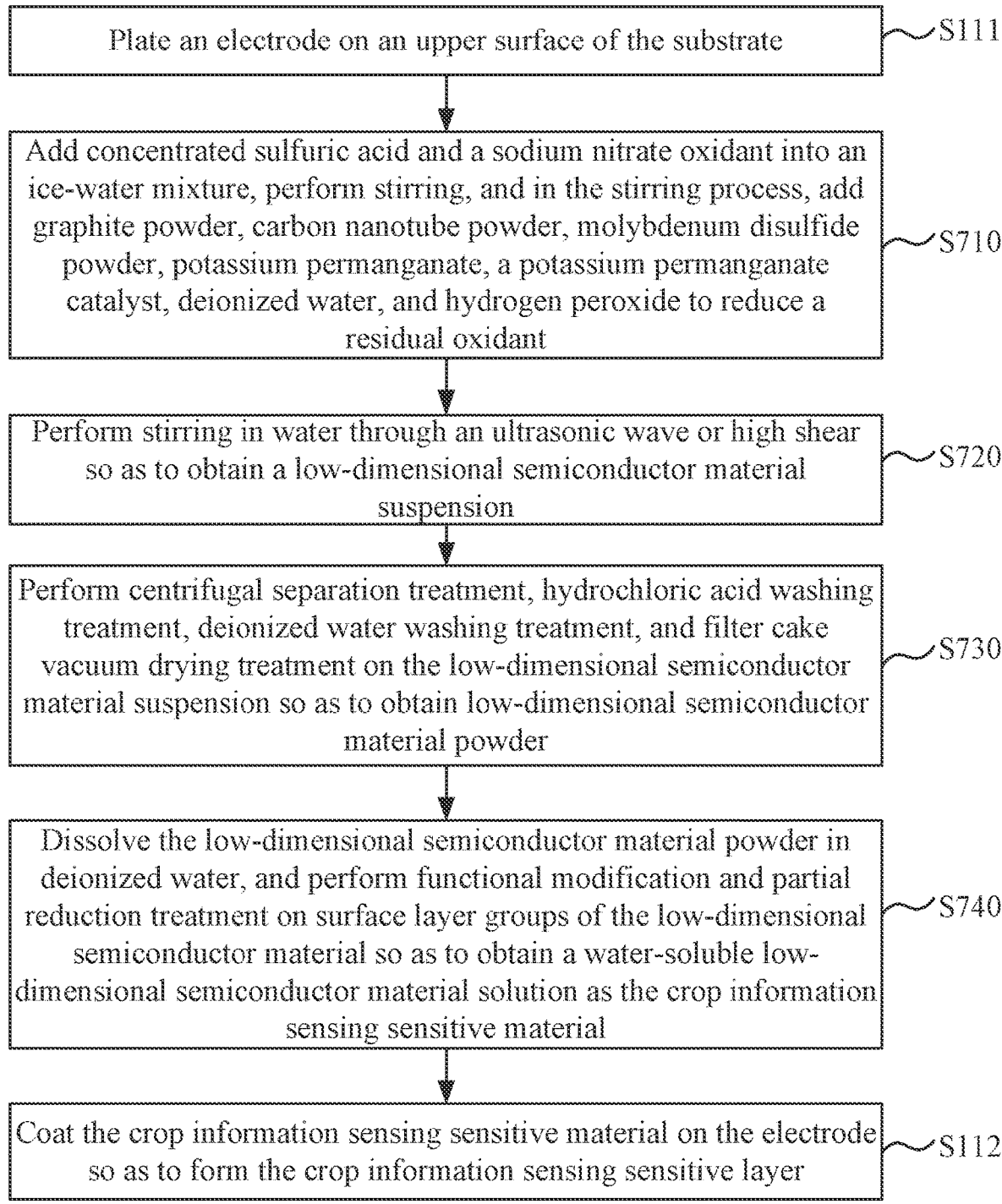
FIG. 5C is a flowchart of a method for manufacturing a crop growth information monitoring device according to another alternative of embodiment three of the present disclosure.
Figure 6:
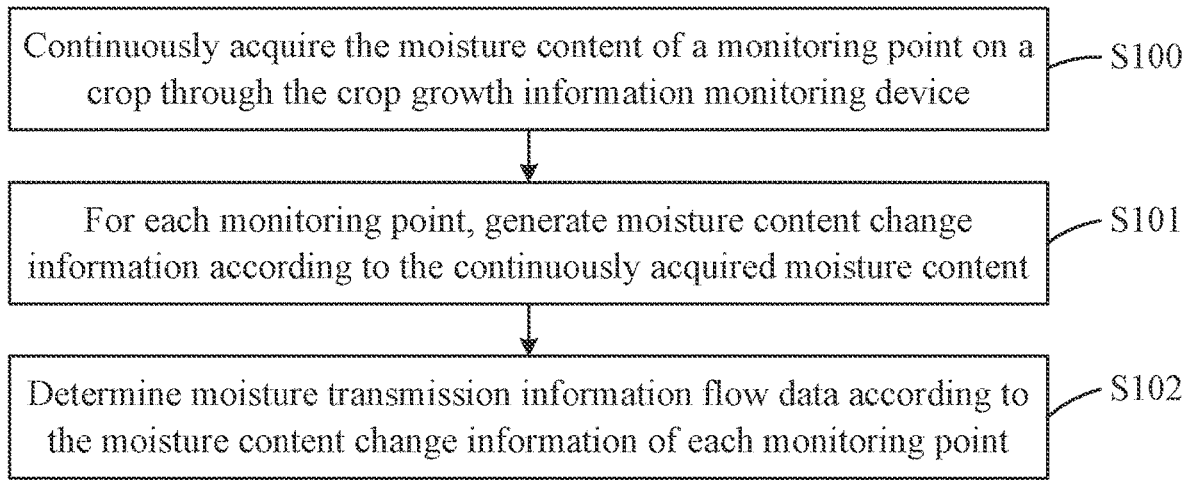
FIG. 6 is a flowchart of a crop growth information monitoring method according to an embodiment of the present disclosure.

As shown in FIG. 5C, in an alternative embodiment, before step S112, the method includes the steps described below.

In S710, concentrated sulfuric acid and a sodium nitrate oxidant are added into an ice-water mixture, stirring is performed, and in the process of the stirring, graphite powder, carbon nanotube powder, molybdenum disulfide powder, potassium permanganate, a potassium permanganate catalyst, deionized water, and hydrogen peroxide are added to reduce a residual oxidant.

In S720, stirring is performed in water through an ultrasonic wave or high shear so as to obtain a low-dimensional semiconductor material suspension.

In S730, centrifugal separation treatment, hydrochloric acid washing treatment, deionized water washing treatment, and filter cake vacuum drying treatment are performed on the low-dimensional semiconductor material suspension so as to obtain low-dimensional semiconductor material powder.

In S740, the low-dimensional semiconductor material powder is dissolved in deionized water, and functional modification and partial reduction treatment are performed on surface layer groups of the low-dimensional semiconductor material so as to obtain a water-soluble low-dimensional semiconductor material solution as the crop information sensing sensitive material.

In an embodiment, the crop information sensing sensitive material is a low-dimensional semiconductor material; the low-dimensional semiconductor material includes at least one of: a functionally modified molybdenum disulfide material, a functionally modified graphene oxide material, a functionally modified carbon nanotube material, or a functionally modified fullerene, and before the crop information sensing sensitive material is coated on the electrode, the method further includes the steps described below.

Concentrated sulfuric acid and a sodium nitrate oxidant are added into an ice-water mixture, stirring is performed, and in the process of the stirring, graphite powder, carbon nanotube powder, molybdenum disulfide powder, fullerene, potassium permanganate, a potassium permanganate catalyst, deionized water, and hydrogen peroxide are added to reduce a residual oxidant.

Stirring is performed in water through an ultrasonic wave or high shear so as to obtain a low-dimensional semiconductor material suspension. Centrifugal separation treatment, hydrochloric acid washing treatment, deionized water washing treatment, and filter cake vacuum drying treatment are performed on the low-dimensional semiconductor material suspension so as to obtain low-dimensional semiconductor material powder.

The low-dimensional semiconductor material powder is dissolved in deionized water, and functional modification and partial reduction treatment are performed on surface layer groups of the low-dimensional semiconductor material so as to obtain a water-soluble low-dimensional semiconductor material solution as the crop information sensing sensitive material.

In an embodiment, after the power supply module is acquired, the method further includes the steps described below.

Referring to FIGS. 2A to 2B, the circuit module 14 in this embodiment is disposed on the bottom surface of the substrate 10, and an electrical connection is established between the circuit module 14 and the electrode 11 through a wire 15. In an embodiment, the electrical parameter signal collection module is first acquired, and the electrical connection is established between the electrical parameter signal collection module and the electrode; then, the signal conditioning circuit module is acquired and disposed on the lower surface of the substrate, and the electrical connection is established between the signal conditioning circuit module and the electrical parameter signal collection module. Alternatively, the step of correspondingly connecting the power supply module to the circuit module may further be included.

According to the embodiments, the circuit module is disposed on the bottom surface of the substrate so that the circuit module and the substrate may be integrated into one device, thus improving the integration of the crop growth information monitoring device.

According to the crop growth information monitoring device manufactured by using the method for manufacturing the crop growth information monitoring device provided in the embodiments of the present disclosure, the air exchange channel support is placed on the surface of the crop, the water molecule information of the crop can be determined according to the molecule concentration capture signal of the crop captured by the crop information sensing sensitive layer, and the air channel is established between the crop information sensing sensitive layer and the surface of the crop through the air exchange channel support, thus improving the accuracy of water molecule information.

Embodiment Four

Embodiment four of the present disclosure provides a crop growth information monitoring method. The method includes attaching and mounting the crop growth information monitoring device provided in any preceding embodiment to a surface of crop tissue and collecting a molecule concentration capture signal through the crop information sensing sensitive layer of the crop growth information monitoring device. In an embodiment, a temperature signal collected by the temperature collection unit may also be acquired, and corresponding molecule information is determined from a pre-stored moisture-electrical parameter-temperature information correspondence according to the molecule concentration capture signal, and the temperature signal collected by the temperature collection unit. In this embodiment, the crop information sensing sensitive layer may perform functional modification and cutting on a chemical group according to an information transformation of a sensed object so as to nondestructively detect and capture one or more of the following pieces of information of leaves, fruits, and other crop tissue: the physiological and biochemical reaction, the photosynthetic rate, the nutrition information, the hormone release information, the information about VOCs, the pesticide residue information, or the disease and insect pest information. The crop information sensing sensitive layer not only detects and captures the water molecule but also may perform the functional modification and cutting on the chemical group according to the information transformation of the sensed object so as to nondestructively detect and capture one or more following pieces of information of the crop tissue: the nutrition information, the hormone release information, the information about VOCs, or the pesticide residue information. For implementations, reference may be made to the preceding relevant description and repetition is not made herein. According to the crop growth information monitoring method provided in the embodiments of the present disclosure, the air exchange channel support is placed on the surface of the crop, and the water molecule information of the crop may be determined according to the molecule concentration capture signal of the crop captured by the crop information sensing sensitive layer, thus improving the accuracy of the water molecule information.

Embodiment Five

Referring to FIGS. 6 to 10, FIG. 6 is a flowchart of a crop growth information monitoring method according to an embodiment of the present disclosure. The method may be performed by a crop growth information monitoring device which may be implemented by software and/or hardware and may be integrated on a hardware platform. The method includes the steps described below.

In S100, moisture content of a monitoring point on a crop is continuously acquired through the crop growth information monitoring device, at least, two monitoring points are arranged on each crop, and each monitoring point is correspondingly provided with the crop growth information monitoring device.

Figure 9:
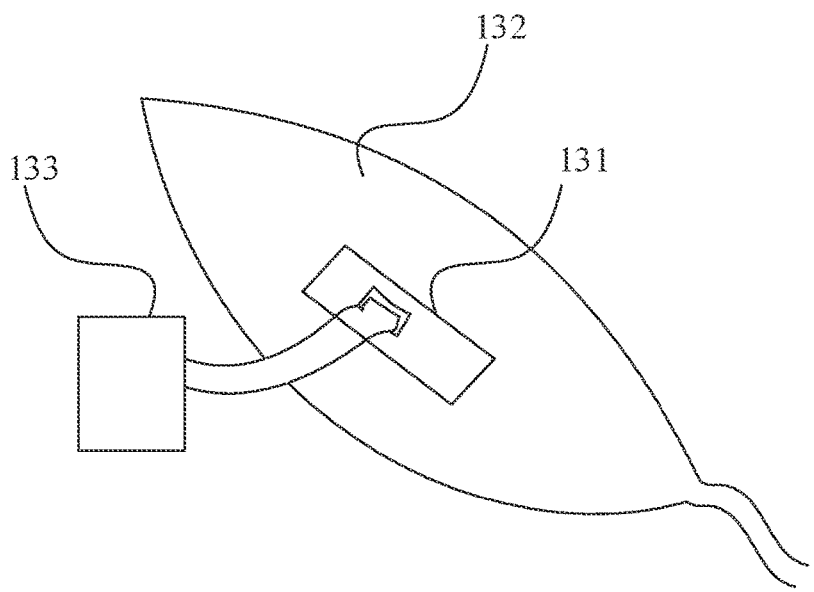
FIG. 9 is a schematic diagram in which a micro flexible sensor for nondestructive monitoring of moisture is attached to a plant leaf surface to perform monitoring according to an embodiment of the present disclosure.

In this embodiment, the crop growth information monitoring device may be a micro flexible sensor for nondestructive monitoring of moisture manufactured by using novel functionalized modified nano-composite materials and a micro-nano processing process, the crop growth information monitoring device may be placed at one or more monitoring points on the surface of the crop, and the crop growth information monitoring device may collect the moisture content at positions corresponding to the monitoring points of the crop. Referring to FIG. 9, a micro flexible sensor 131 for nondestructive monitoring of moisture is used as the crop growth information monitoring device in an embodiment and attached to a plant leaf surface 132, and monitoring signals of the micro flexible sensor 131 for nondestructive monitoring of moisture is connected to a monitoring data processing server 133 via a wire.

Figure 7:
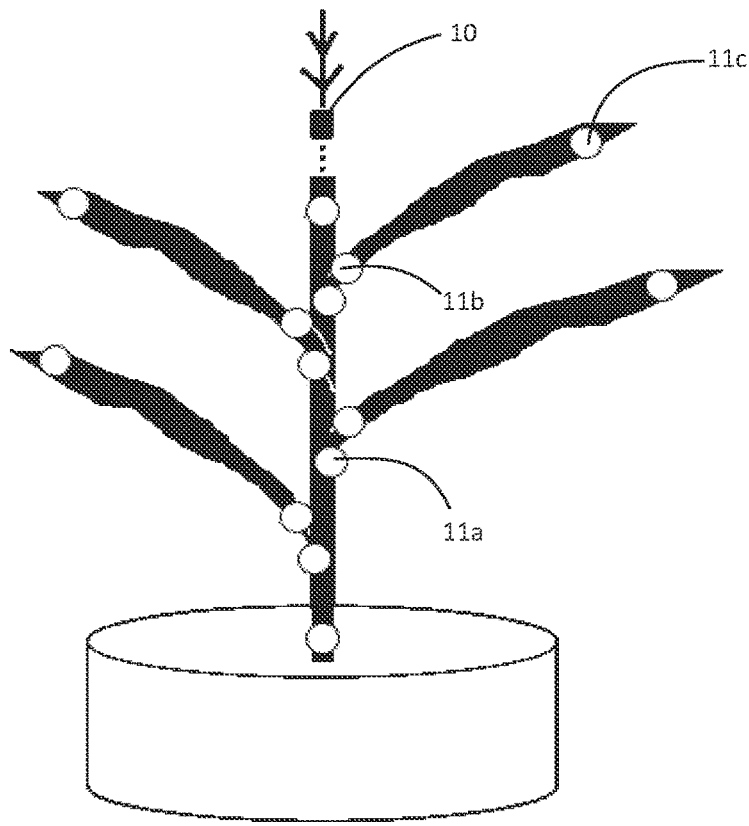
FIG. 7 is a schematic diagram illustrating a scenario of a crop growth information monitoring method according to an embodiment of the present disclosure.

At least two monitoring points are arranged on each crop and are respectively arranged at different parts of the crop. Each monitoring point is correspondingly provided with the crop growth information monitoring device so as to collect the moisture content at such monitoring point. FIG. 7 is a schematic diagram illustrating a scenario of a crop growth information monitoring method according to an embodiment of the present disclosure. Exemplarily, as shown in FIG. 7, a crop 10 includes parts such as a stem and a leaf, several monitoring points 11$a$ may be arranged on the stem, corresponding monitoring points may be arranged on the leaf, and crop growth information monitoring devices corresponding to the multiple monitoring points are numbered. A plurality of monitoring points may also be arranged on the same part; exemplarily, monitoring points 11$b$ and 11$c$ may be arranged at the base and apex of the leaf, respectively.

Since the distances between different parts of the crop and the root of the crop are different, the degrees of water evaporation at different parts are also different. Therefore, it is necessary to arrange a plurality of monitoring points at different parts of the crop so as to collect the moisture content at different parts of the crop.

In an embodiment, the crop growth information monitoring device may also be calibrated before being used for continuously acquiring the moisture content of the monitoring point on the crop, and the steps described below may be included.

Figure 10:
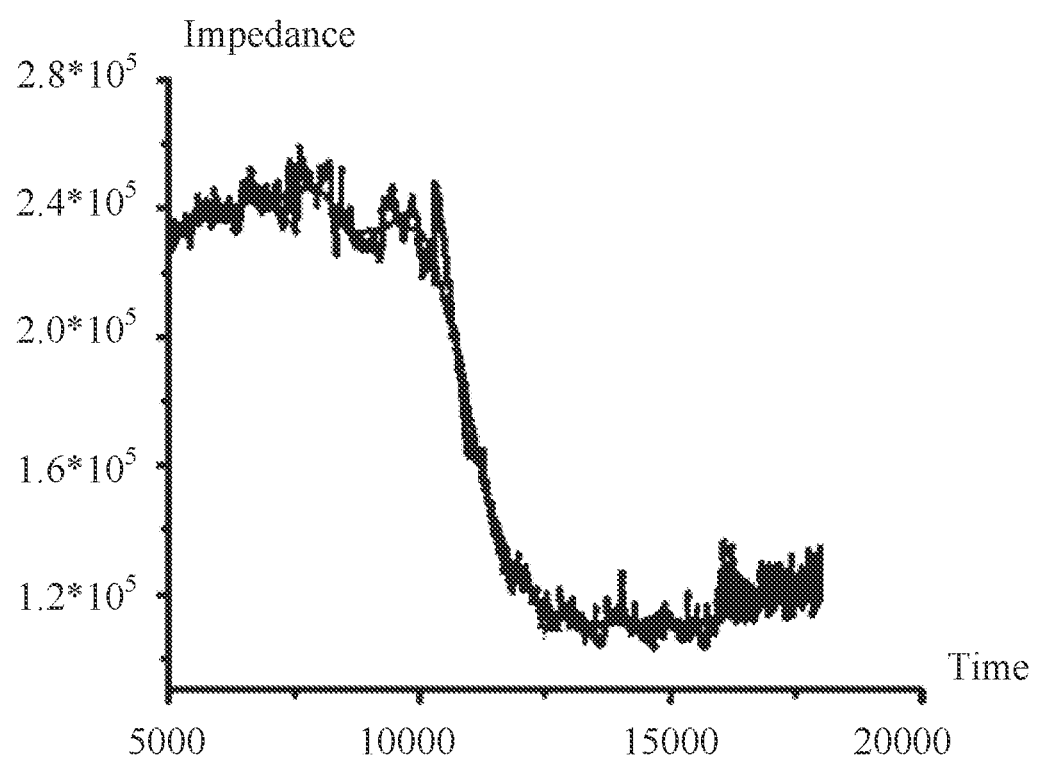
FIG. 10 is a schematic diagram of a monitoring reference line of a moisture transmission information flow according to an embodiment of the present disclosure.

A sensor of the crop growth information monitoring device is calibrated to acquire reference moisture content $\eta$ corresponding to a monitoring point of the crop. The reference moisture content $\eta$ is the optimal moisture content of plant tissue for healthy growth of a plant, and the reference moisture content is set as a reference value of the crop growth information monitoring device. In an embodiment, a monitoring reference line $\tau$ of the crop growth information monitoring device with respect to a moisture transmission information flow is determined according to the reference moisture content $\eta$, where $\tau f(\eta)$. In an embodiment, a monitoring reference line with respect to a moisture transmission information flow is as shown in FIG. 10. Processing such as fitting and smoothing is performed on $\eta$ and $\tau$ actually detected at the monitoring points of the crop in FIG. 10, so that the monitoring reference line with respect to the moisture transmission information flow may be obtained.

In an embodiment, the reference moisture content is reference moisture content at any part of the crop, and the reference value of the crop growth information monitoring device for monitoring any part is calibrated according to the reference moisture content of the part, so that the monitoring accuracy of the crop growth information monitoring device can be improved.

In an embodiment, the reference moisture content is leaf moisture content of a leaf on a crop, and accordingly, the leaf moisture content may be set as the reference value of the crop growth information monitoring device.

The leaf moisture content may be acquired according to a slice weighing method. Exemplarily, a leaf on a crop consistent with a leaf to be monitored is selected, picked, and weighed so that a leaf fresh weight of the leaf is acquired; then, the leaf is baked to dry the moisture in the leaf. After being dried for 24 hours, the leaf is weighed so that the leaf dry weight is obtained. The leaf moisture content of the crop is calculated according to the leaf fresh weight and the leaf dry weight, and the leaf moisture content=(leaf fresh weight−leaf dry weight/leaf fresh weight×100%.

After the leaf moisture content is obtained, the crop growth information monitoring device may be calibrated according to the leaf moisture content. The leaf moisture content may be set as the reference value of the crop growth information monitoring device, that is, the leaf moisture content is set as the initial moisture content measured by the crop growth information monitoring device arranged on the leaf to be monitored.

In S101, for each monitoring point, moisture content change information is generated according to continuously acquired moisture content. In an embodiment, the moisture content change information is information about a moisture content change over time at a monitoring point and may exemplarily be a moisture content change curve. After irrigation treatment is performed on the crop, the moisture content of the monitoring point on the crop gradually increases with time, and after the irrigation, the moisture content of the monitoring point gradually decreases with crop transpiration.

The moisture content change information is generated according to the continuously acquired moisture content and may reflect the internal moisture status of the crop at different time points, and thus required information may be extracted from the moisture change information.

In S102, moisture transmission information flow data is determined according to the moisture content change information of each monitoring point, where the moisture transmission information flow data includes a moisture transmission rate between any two monitoring points and a moisture absorption amount of the crop in any time period.

The moisture transmission information flow data is data reflecting the change information about the moisture within the crop and the status of the moisture within the crop. The moisture change information includes the movement information about moisture within the crop and may be the moisture transmission rate between any two monitoring points. The status of moisture within the crop is the moisture absorption amount of the crop in any time period.

After the crop is irrigated, moisture is absorbed from the root of the crop and gradually transmitted upward along the stem of the crop and to the leaves. The transmission rates of moisture moving in the crop are different for different states of the crop. Exemplarily, a low moisture transmission rate within the crop may indicate that the vitality of the root of the crop is low or that the crop has a disease problem. The moisture content in the crop may also reflect the state of the crop, exemplarily, if the moisture content of the crop does not increase after the crop is irrigated, the crop may have a disease problem and the like.

The moisture transmission rate between any two monitoring points may be determined according to the change in the moisture content of the two monitoring points within a preset time period. After the crop is irrigated, the moisture is transmitted within the crop and the moisture transmission rate is determined according to the change in the moisture content measured at the two monitoring points through which the moisture passes successively in the transmission.

Figure 8:
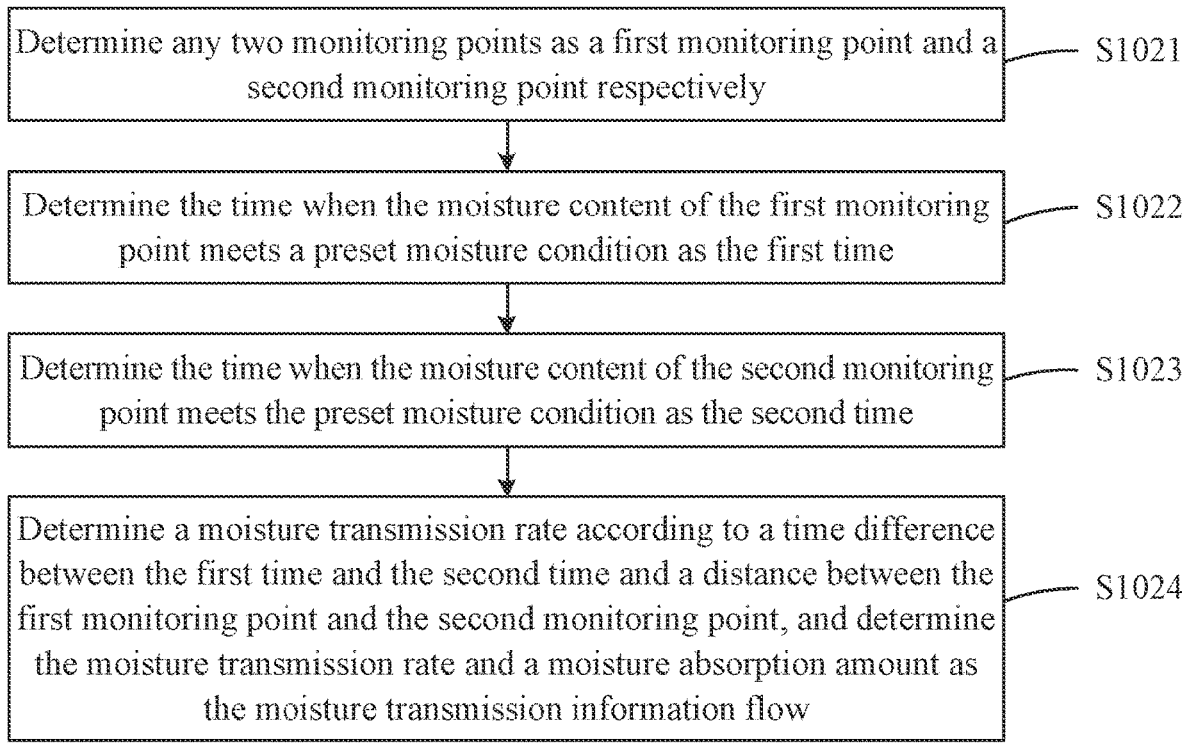
FIG. 8 is a flowchart of another crop growth information monitoring method according to an embodiment of the present disclosure.

In an embodiment, as shown in FIG. 8, the step of determining the moisture transmission information flow data according to the moisture content change information of each monitoring point may be performed in the manner described below.

In S1021, any two monitoring points are determined and are used as a first monitoring point and a second monitoring point respectively.

In an embodiment, any two monitoring points may be two monitoring points located at the same part of the crop or two monitoring points located at different parts. Exemplarily, the first monitoring point may be a monitoring point on the stem of the crop closest to the root, and the second monitoring point may be a higher monitoring point on the stem of the crop, and the transmission rate of moisture on the stem may be obtained according to the two monitoring points. The first monitoring point and the second monitoring point are two monitoring points through which moisture passes successively in the transmission.

In S1022, the time when the moisture content of the first monitoring point meets a preset moisture condition is determined as the first time.

The preset moisture condition may be a case where the monitored moisture content abruptly changes, exemplarily, if the moisture content of the monitoring point increases by an amount greater than a first threshold within the first time period, it is determined that the moisture content of the first monitoring point meets the preset moisture condition, that is, the moisture content of the monitoring point abruptly changes. If the moisture content of the first monitoring point meets the preset moisture condition, the moisture is transmitted from the root to the first monitoring point, and the current time is recorded as the first time.

In S1023, the time when the moisture content of the second monitoring point meets a preset moisture condition is determined as the second time.

If the moisture content of the second monitoring point meets the preset moisture condition, the moisture is transmitted from the root to the second monitoring point, and the current time is recorded as the second time.

In S1024, a moisture transmission rate and a moisture absorption amount are determined according to a time difference between the first time and the second time and a distance between the first monitoring point and the second monitoring point and are determined as the moisture transmission information flow.

The distance is a transmission distance of moisture within the crop. Exemplarily, if the second monitoring point is the apex of the leaf and the first monitoring point is a monitoring point on the stem, the distance is a sum of the length of the leaf where the second monitoring point is located and the distance from the base of the leaf where the second monitoring point is located to the first monitoring; point.

The moisture transmission rate V is equal to (L2−L1)/(T2−T1), where L2 denotes the distance from the second monitoring point to the root of the crop, L1 denotes the distance from the first monitoring point to the root of the crop, T2 denotes the second time, and T1 denotes the first time.

According to the preceding operations, the moisture transmission rate between any two monitoring points may be obtained, that is, the moisture transmission rates at different parts of the crop may be obtained and determined as the moisture transmission information flow.

In this embodiment, according to the monitored moisture transmission information flow, a plant health index, a moisture profit and loss index, an irrigation index, and a drainage index may be constructed to guide and control an execution device such as an irrigation device, a fertilization device, or a drainage device to perform an intelligent operation. The intelligent operation includes irrigation, drainage, or other related operations.

The moisture absorption amount of the crop in any time period may be the moisture absorption amount of the whole crop in any time period, may include the moisture absorption amount of all leaves of the crop in any time period, and may also include the moisture absorption amount of the stem of the crop in any time period.

For each monitoring point, the moisture absorption amount of the crop in any time period may be calculated according to the moisture content measured in any time period at each monitoring point. Exemplarily, a time period is selected, the crop growth information monitoring device arranged on the leaf of the crop monitors the moisture content of the leaf of the crop at a plurality of time points in the time period, at least the moisture content at the starting point and the moisture content at the ending point of the time period are monitored, then the moisture content of the crop at the starting point and the moisture content of the crop at the ending point may be calculated according to the moisture content, and the moisture absorption amount of the crop in the time period may be obtained according to the moisture content at the starting point and at the ending point.

In an embodiment, the moisture content of the monitoring point monitored by the crop growth information monitoring device is the moisture content at the position where the monitoring point is located, and reference moisture content of the crop may be calculated according to the moisture content at the position where the monitoring point is located. The reference moisture content may be the moisture content within one unit; exemplarily, for the moisture content of the leaf of the crop, the reference moisture content may be the moisture content within one square centimeter. The moisture content of the whole leaf may be calculated according to the reference moisture content. According to the moisture content of the leaf at two time points, the moisture absorption amount of the leaf within this period may be obtained.

The moisture absorption amount of the stem of the crop may also be calculated according to the moisture absorption amount of the whole plant and may also be calculated in the preceding manner, and then the moisture absorption amount of the whole crop within any time period may be obtained.

According to the moisture transmission information flow data determined according to the moisture content change information of each monitoring point, the moisture statuses of different parts of the crop and the whole crop within different periods may be obtained, and thus the administrator can monitor and manage the crop according to the moisture transmission information flow data.

In an embodiment, the method further includes the step described below while continuously acquiring the moisture content of the monitoring points on the crop.

The element content of the monitoring points on the crop is continuously acquired through an element monitoring device.

The element content may be continuously acquired through the element monitoring device arranged on the surface of the crop. The element content is the content of an element contained in the moisture. The element content includes at least one of the heavy-metal content, the pesticide content, or the nutrient-solution content. Accordingly, the element monitoring device is at least one of a heavy-metal monitoring device, a pesticide monitoring device, or a nutrient-solution monitoring device. The heavy-metal monitoring device is made of a heavy-metal sensitive material, the pesticide monitoring device is made of a pesticide-residue sensing sensitive material, and the nutrient-solution monitoring device is made of a nutrient sensitive material.

Accordingly, element content change information is generated according to the continuously acquired element content, and element information flow data is determined according to the element content change information of each monitoring point. The element information flow data includes an element transmission rate between any two monitoring points and an element absorption amount of the crop in any time period.

The element content of the monitoring point on the crop may be continuously acquired through the element monitoring device so that the element information flow data of the crop may be obtained and the statuses of various elements at different parts of the crop and the whole crop in different periods may be obtained, which can assist the administrator in monitoring and managing the crop.

According to the embodiments of the present disclosure, the moisture content of the monitoring point on the crop is continuously acquired by the crop growth information monitoring device; for each monitoring point, moisture content change information is generated according to the continuously acquired moisture content; and moisture transmission information flow data is determined according to the moisture content change information of each monitoring point. The moisture transmission information flow data includes the moisture transmission rate between any two monitoring points and the moisture absorption amount of the crop in any time period. According to the embodiments of the present disclosure, the moisture statuses of different parts of the crop and the whole crop in different periods may be obtained according to the moisture content of different monitoring points on the monitored crop, more accurate moisture information can be obtained, low in cost and simple in operation.

What is claimed is:

1. A crop growth information monitoring device, comprising: an air exchange channel support, a crop information sensing sensitive layer, an electrode, and a substrate;
wherein the air exchange channel support is disposed on the substrate, and in a case where the air exchange channel support is in contact with a monitoring point on a surface of a crop, a gas exchange channel is formed between the crop information sensing sensitive layer and the surface of the crop;
the crop information sensing sensitive layer is configured to sense information about a molecule emitted through crop transpiration so as to generate a molecule concentration capture signal; and
the electrode is plated on an upper surface of the substrate, and the crop information sensing sensitive layer is coated on the electrode;
wherein the crop growth information monitoring device further comprises an electrical parameter signal collection module and a signal conditioning circuit module,
wherein the electrical parameter signal collection module is configured to receive through the electrode the molecule concentration capture signal collected by the crop information sensing sensitive layer and convert the molecule concentration capture signal into an electrical signal by using an electrical parameter-molecule concentration adsorption and desorption physical and chemical effect of the crop information sensing sensitive layer; and the signal conditioning circuit module comprises a temperature collection unit, a signal processing unit, and a signal sending unit;
wherein the temperature collection unit is configured to collect a temperature of the monitoring point of the crop so as to generate a temperature signal; the signal processing unit is configured to determine, according to the molecule concentration capture signal, and the temperature signal collected by the temperature collection unit, molecule concentration information from a pre-stored molecule concentration-electrical parameter-temperature information correspondence;
and the signal sending unit is configured to send the molecule concentration information generated by the signal processing unit to a server terminal.

2. The device of claim 1, further comprising: a power supply module, wherein the power supply module comprises a storage battery and a solar powered device; and
the solar powered device is configured to convert solar energy into electrical energy and store the electrical energy in the storage battery.

3. A method for manufacturing a crop growth information monitoring device, comprising:
acquiring a substrate;
plating an electrode on an upper surface of the substrate;
coating a crop information sensing sensitive material on the electrode so as to form a crop information sensing sensitive layer, wherein the crop information sensing sensitive layer is configured to sense information about a molecule emitted through crop transpiration so as to generate a molecule concentration capture signal;
performing heat treatment on the substrate; and
mounting an air exchange channel support on the upper surface of the substrate, and in a case where the air exchange channel support is in contact with a monitoring point on a surface of a crop, forming a gas exchange channel between the crop information sensing sensitive layer and the surface of the crop;
wherein the crop information sensing sensitive material is a low-dimensional semiconductor material; the low-dimensional semiconductor material comprises at least one of: a functionally modified molybdenum disulfide material, a functionally modified graphene oxide material, a functionally modified carbon nanotube material, or a functionally modified fullerene; and
before coating the crop information sensing sensitive material on the electrode, the method further comprises:
adding concentrated sulfuric acid and a sodium nitrate oxidant to an ice-water mixture, performing stirring, and in a process of the stirring, adding graphite powder, carbon nanotube powder, molybdenum disulfide powder, fullerene, potassium permanganate, a potassium permanganate catalyst, deionized water, and hydrogen peroxide to reduce a residual oxidant;
performing stirring in water through an ultrasonic wave or high shear so as to obtain a low-dimensional semiconductor material suspension;
performing centrifugal separation treatment, hydrochloric acid washing treatment, deionized water washing treatment, and filter cake vacuum drying treatment on the low-dimensional semiconductor material suspension so as to obtain low-dimensional semiconductor material powder; and
dissolving the low-dimensional semiconductor material powder in deionized water, and performing functional modification and partial reduction treatment on surface layer groups of the low-dimensional semiconductor material so as to obtain a water-soluble low-dimensional semiconductor material solution as the crop information sensing sensitive material.

4. The method of claim 3, further comprising:

acquiring an electrical parameter signal collection module, and establishing an electrical connection between the electrical parameter signal collection module and the electrode;

acquiring a signal conditioning circuit module, disposing the signal conditioning circuit module on a lower surface of the substrate, and establishing an electrical connection between the signal conditioning circuit module and the electrical parameter signal collection module; and acquiring a power supply module.

5. The method of claim 3, wherein the substrate is a flexible printed circuit (FPC), a polyimide film, a polyester film, a flexible film, a silicon wafer, a silicon dioxide wafer, or a ceramic wafer; and before acquiring the substrate, the method further comprises:

cutting the substrate, performing ultrasonic cleaning by using acetone, absolute ethyl alcohol, and deionized water separately, and performing nitrogen drying.

6. A crop growth information monitoring method, comprising: attaching and mounting a crop growth information monitoring device to a surface of crop tissue, and sensing information about a molecular released by the crop tissue through a crop information sensing sensitive layer of the crop growth information monitoring device so as to generate a molecule concentration capture signal;

wherein the crop growth information monitoring device comprises an air exchange channel support, the crop information sensing sensitive layer, an electrode, a substrate, an electrical parameter signal collection module, and a signal conditioning circuit module;

wherein the air exchange channel support is disposed on the substrate, and in a case where the air exchange channel support is in contact with a monitoring point on a surface of a crop, a gas exchange channel is formed between the crop information sensing sensitive layer and the surface of the crop; the crop information sensing sensitive layer is configured to sense information about a molecule emitted through crop transpiration so as to generate a molecule concentration capture signal; the electrode is plated on an upper surface of the substrate, and the crop information sensing sensitive layer is coated on the electrode;

the electrical parameter signal collection module is configured to receive through the electrode the molecule concentration capture signal collected by the crop information sensing sensitive layer and convert the molecule concentration capture signal into an electrical signal by using an electrical parameter-molecule concentration adsorption and desorption physical and chemical effect of the crop information sensing sensitive layer; and the signal conditioning circuit module comprises a temperature collection unit, a signal processing unit, and a signal sending unit;

wherein the temperature collection unit is configured to collect a temperature of the monitoring point of the crop so as to generate a temperature signal; the signal processing unit is configured to determine, according to the molecule concentration capture signal, and the temperature signal collected by the temperature collection unit, molecule concentration information from a pre-stored molecule concentration-electrical parameter-temperature information correspondence;

and the signal sending unit is configured to send the molecule concentration information generated by the signal processing unit to a server terminal.

7. The method of claim 6, comprising: performing, by the crop information sensing sensitive layer according to a transformation of one of a sensed object or a sensing parameter index, functional modification and cutting on a targeted chemical group;

and combining different modification groups to simultaneously and nondestructively detect and capture at least one of the followings of the crop tissue: a physiological and biochemical reaction, a photosynthetic rate, nutrition information, hormone release information, information about volatile organic compounds (VOCs), pesticide residue information, or disease and insect pest information.

8. The method of claim 6, wherein the crop growth information monitoring device further comprises a power supply module, wherein the power supply module comprises a storage battery and a solar powered device; and the solar powered device is configured to convert solar energy into electrical energy and store the electrical energy in the storage battery.

* * * * *